United States Patent [19]

Takaya et al.

[11] Patent Number: 5,210,080
[45] Date of Patent: * May 11, 1993

[54] CEPHEM COMPOUNDS

[75] Inventors: Takao Takaya, Kawanishi; Kazuo Sakane, Kawanishi; Kenzi Miyai, Kawanishi; Kohji Kawabata, Osaka, all of Japan

[73] Assignee: Fujisawa Pharmaceutical Co., Ltd., Osaka, Japan

[*] Notice: The portion of the term of this patent subsequent to Apr. 9, 2008 has been disclaimed.

[21] Appl. No.: 683,473

[22] Filed: Apr. 9, 1991

Related U.S. Application Data

[63] Continuation of Ser. No. 238,136, Aug. 30, 1988, abandoned.

[30] Foreign Application Priority Data

Sep. 7, 1987 [GB] United Kingdom ............... 8721016

[51] Int. Cl.⁵ ................ C07D 501/46; A61K 31/545
[52] U.S. Cl. ..................................... 514/202; 540/222
[58] Field of Search ............... 540/227, 222; 514/202

[56] References Cited

U.S. PATENT DOCUMENTS

| | | | |
|---|---|---|---|
| 4,748,171 | 5/1988 | Yamauchi et al. | 540/222 |
| 4,927,818 | 5/1990 | Takaya et al. | 540/222 |
| 5,108,997 | 4/1992 | Takaya et al. | 540/222 |

FOREIGN PATENT DOCUMENTS

| | | |
|---|---|---|
| 0062321 | 10/1982 | European Pat. Off. |
| 0223246 | 5/1987 | European Pat. Off. |
| 8106321 | 7/1982 | South Africa |
| 2037281 | 7/1980 | United Kingdom |

*Primary Examiner*—Nicholas S. Rizzo
*Attorney, Agent, or Firm*—Oblon, Spivak, McClelland, Maier & Neustadt

[57] ABSTRACT

The invention relates to compounds of antimicrobial activity, of the formula

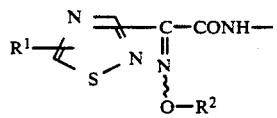

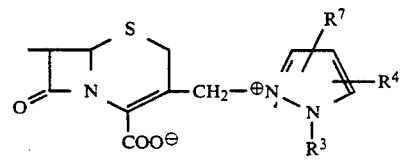

wherein
$R^1$ is amino or protected amino,
$R^2$ is lower alkyl or lower alkenyl,
$R^3$ is lower alkyl, hydroxy(lower)alkyl or protected hydroxy(lower)alkyl,
$R^4$ is amino, protected amino, lower alkylamino, protected lower alkylamino, carboxy(lower)alkylamino, N-[protected carboxy(lower)alkyl]amino and
$R^7$ is hydrogen or lower alkyl, or
a pharmaceutically acceptable salt thereof.

8 Claims, No Drawings

CEPHEM COMPOUNDS

This application is a continuation of application Ser. No. 07/238,136, filed on Aug. 30, 1988, now abandoned.

The present invention relates to new cephem compounds and pharmaceutically acceptable salts thereof. More particularly, it relates to new cephem compounds and pharmaceutically acceptable salts thereof, which have antimicrobial activities, to processes for preparation thereof, to pharmaceutical composition comprising the same, and to a method for treating infectious diseases in human being and animals.

Accordingly, one object of the present invention is to provide the cephem compounds and pharmaceutically acceptable salts thereof, which are highly active against a number of pathogenic microorganisms.

Another object of the present invention is to provide processes for the preparation of the cephem compounds and salts thereof.

A further object of the present invention is to provide pharmaceutical composition comprising, as an active ingredient, said cephem compounds or their pharmaceutically acceptable salts.

Still further object of the present invention is to provide a method for treating infectious diseases caused by pathogenic microorganisms, which comprises administering said cephem compounds to infected human being or animals.

The object cephem compounds of the present invention are novel and can be represented by the following general formula [I]:

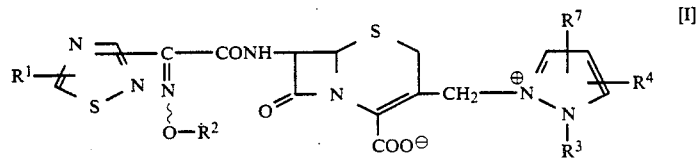

wherein
R¹ is amino or protected amino,
R² is lower alkyl or lower alkenyl,
R³ is lower alkyl, hydroxy(lower)alkyl or protected hydroxy(lower)alkyl,
R⁴ is amino, protected amino, lower alkylamino, protected lower alkylamino, carboxy(lower)alkylamino, N-[protected carboxy(lower)alkyl]amino, and
R⁷ is hydrogen or lower alkyl.

As to the object compound [I], the following points are to be noted.

That is, the object compound [I] includes syn isomer, anti isomer and a mixture thereof. Syn isomer means one geometrical isomer having the partial structure represented by the following formula:

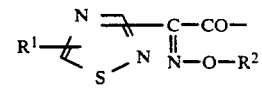

(wherein R¹ and R² are each as defined above) and anti isomer means the other geometrical isomer having the partial structure represented by the following formula:

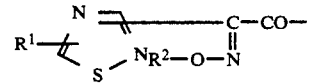

(wherein R¹ and R² are each as defined above), and all of such geometrical isomers and mixture thereof are included within the scope of this invention.

In the present specification and claim, the partial structure of these geometrical isomers and mixture thereof are represented for convenient sake by the following formula:

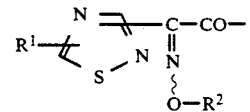

(wherein R¹ and R² are each as defined above).

Another point to be noted is that the pyrazolio moiety of the compound [I] can also exist in the tautomeric form, and such tautomeric equilibrium can be represented by the following schemes.

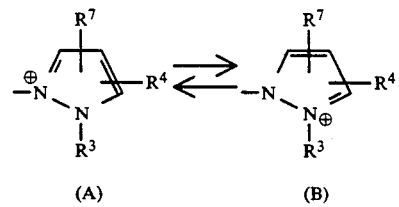

(wherein R³, R⁴ and R⁷ are each as defined above).

Both of the above tautomeric isomers are included within the scope of the present invention, and in the present specification and claim, however, the object compound [I] is represented for the convenient sake by one expression of the pyrazolio group of the formula (A).

The cephem compound [I] of the present invention can be prepared by processes as illustrated in the following.

Process 1

-continued

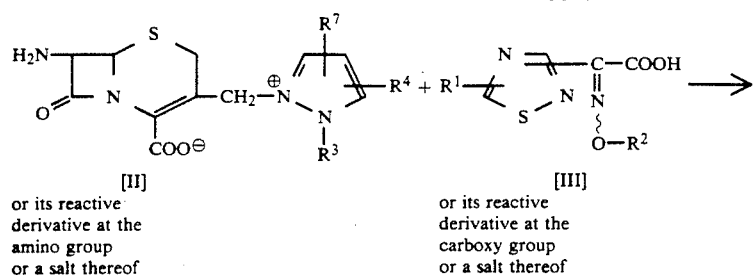

[II]
or its reactive
derivative at the
amino group
or a salt thereof

[III]
or its reactive
derivative at the
carboxy group
or a salt thereof

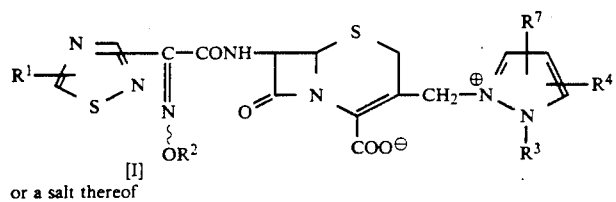

[I]
or a salt thereof

Process 2

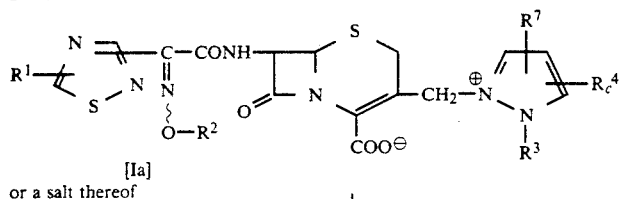

[Ia]
or a salt thereof

↓ Elimination reaction of the carboxy protective group

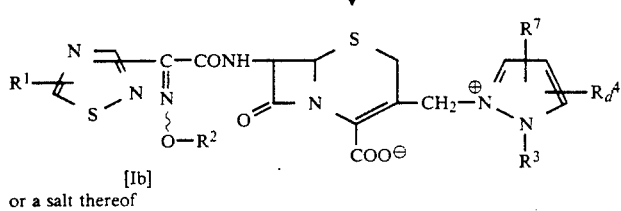

[Ib]
or a salt thereof

Process 3

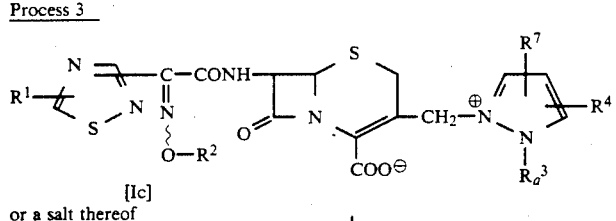

[Ic]
or a salt thereof

↓ Elimination reaction of the hydroxy protective group

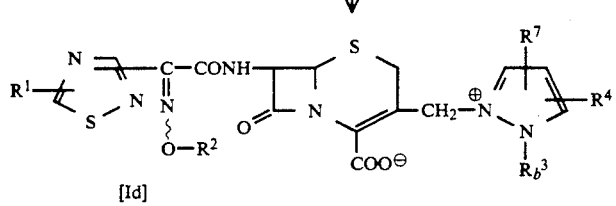

[Id]
or a salt thereof wherein
$R^1$, $R^2$, $R^3$, $R^4$ and $R^7$ are each as defined above,
$R_c^4$ is N-[protected carboxy(lower)alkyl]amino,
$R_d^4$ is carboxy(lower)alkylamino,
$R_a^3$ is protected hydroxy(lower)alkyl, and
$R_b^3$ is hydroxy(lower)alkyl.

The starting compound [II] can be prepared by the following processes.

Process A

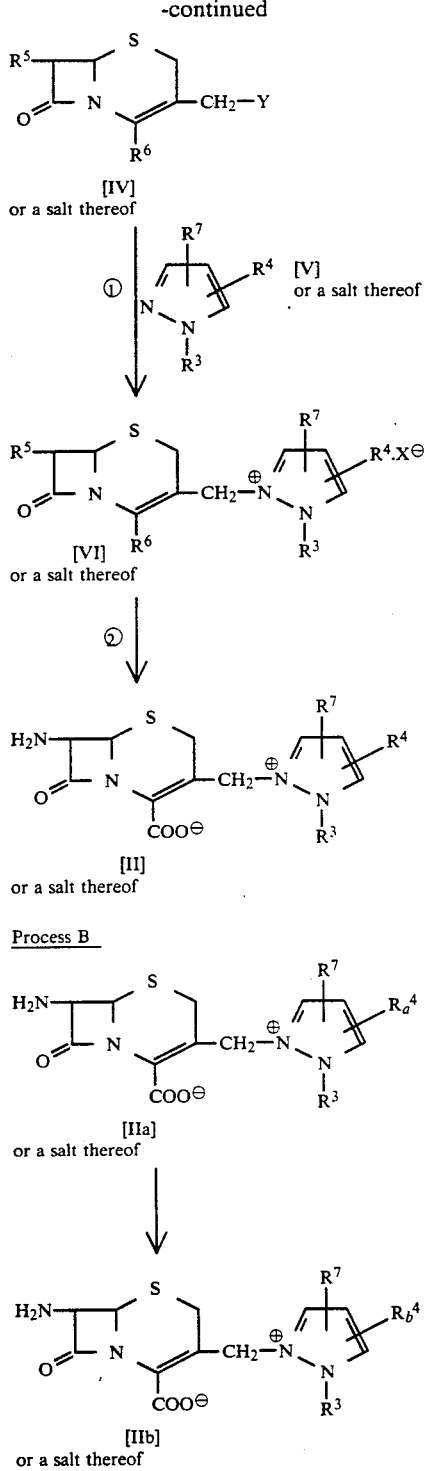

wherein
R³, R⁴ and R⁷ are each as defined above,
R⁵ is protected amino,
R⁶ is protected carboxy,
Y is a leaving group,
X⊖ is an anion,
$R_a^4$ is protected amino or protected lower alkylamino, and
$R_b^4$ is amino or lower alkylamino.

The starting compound [V] or a salt thereof can be prepared by the methods disclosed in the Preparations 1 to 8 described layer or similar manners thereto.

In the above and subsequent descriptions of this specification, suitable examples of the various definitions are explained in detail as follows :

The term "lower" is intended to mean 1 to 6 carbon atom(s), unless otherwise indicated.

Suitable "amino protective group" in the "protected amino" and "protected lower alkylamino" may be an acyl group as mentioned below, substituted or unsubstituted ar(lower)alkylidene [e.g. benzylidene, hydroxybenzylidene, etc.], ar(lower)alkyl such as mono or di or triphenyl(lower)alkyl [e.g. benzyl, phenethyl, benzhydryl, trityl, etc.], or the like.

Suitable "acyl" may be lower alkanoyl [e.g. formyl, acetyl, propionyl, hexanoyl, pivaloyl, etc.], mono(or di or tri)halo(lower)alkanoyl [e.g. chloroacetyl, trifluoroacetyl, etc.], lower alkoxycarbonyl [e.g. methoxy carbonyl, ethoxycarbonyl, tert-butoxycarbonyl, tert-pentyloxycarbonyl, hexyloxycarbonyl, etc.], carbamoyl, aroyl [e.g. benzoyl, toluoyl, naphthoyl, etc.], ar(lower)alkanoyl [e.g. phenylacetyl, phenylpropionyl, etc.], aryloxycarbonyl [e.g. phenoxycarbonyl, naphthyloxycarbonyl, etc.], aryloxy(lower)alkanoyl [e.g. phenoxyacetyl, phenoxypropionyl, etc.], arylglyoxyloyl [e.g. phenylglyoxyloyl, naphthylglyoxyloyl, etc.], ar(lower)alkoxycarbonyl which may have suitable substituent(s) [e.g. benzyloxycarbonyl, phenethyloxycarbonyl, p-nitrobenzyloxycarbonyl, etc.], or the like.

Suitable "lower alkyl" and "lower alkyl moieties" in the "hydroxy(lower)alkyl", "protected hydroxy(lower)alkyl", "lower alkylamino", "protected lower alkylamino", "carboxy(lower)alkylamino" and "N-[protected carboxy(lower)alkyl]amino", may be a straight or branched one such as methyl, ethyl, propyl, isopropyl, butyl, isobutyl, tert-butyl, pentyl, hexyl or the like.

Suitable "lower alkenyl" may be a straight or branched one such as vinyl, allyl, 1-propenyl, isopropenyl, butenyl, isobutenyl, pentenyl, hexenyl or the like.

Suitable "protected hydroxy" in the "protected hydroxy(lower)alkyl" may be acyloxy group or the like. Suitable "acyl moiety" in the "acyloxy" may be lower alkanoyl [e.g. formyl, acetyl, propionyl, hexanoyl, pivaloyl, etc.], mono(or di or tri)halo(lower)alkanoyl [e.g. chloroacetyl, trifluoroacetyl, etc.], lower alkoxycarbonyl [e.g. methoxycarbonyl, ethoxycarbonyl, tert-butoxycarbonyl, tert-pentyloxycarbonyl, hexyloxycarbonyl, etc.], carbamoyl or the like.

Suitable "protected carboxy" and "protected carboxy moiety" in the term "N-[protected carboxy(lower)alkyl]amino" may be an esterified carboxy group, or the like, and concrete examples of the ester moiety in said esterified carboxy group may be the ones such as lower alkyl ester [e.g. methyl ester, ethyl ester, propyl ester, isopropyl ester, butyl ester, isobutyl ester, tert-butyl ester, pentyl ester, hexyl ester, 1-cyclopropylethyl ester, etc.]which may have suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, 1-acetoxyethyl ester, 1-propionyloxyethyl ester, pivaloyloxymethyl ester, 2-propionyloxyethyl ester, hexanoyloxymethyl ester, etc.], lower alkanesulfonyl(lower)alkyl ester [e.g. 2-mesylethyl ester, etc.]or mono(or di or tri)halo(lower)alkyl ester [e.g. 2-iodoethyl ester, 2,2,2-trichloroethyl ester, etc.]; lower alkenyl ester [e.g. vinyl ester, allyl ester, etc.]; lower alkynyl ester [e.g. ethynyl ester, propynyl ester, etc.]; ar(lower)alkyl ester which may have suitable substituent(s) [e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-tert-butylbenzyl ester, etc.]; aryl ester which may have suitable substituent(s) [e.g. phenyl ester, 4-chlorophenyl ester, tolyl ester, 4-tert-butylphenyl ester, xylyl ester, mesityl ester, cumenyl ester, etc.]; or the like.

Suitable "leaving group" may be halogen [e.g. chlorine, bromine, iodine, etc.], acyloxy such as sulfonyloxy [e.g. benzenesulfonyloxy, tosyloxy, mesyloxy, etc.], lower alkanoyloxy [e.g. acetyloxy, propionyloxy, etc.], or the like.

Suitable "anion" may be formate, acetate, trifluoroacetate, maleate, tartrate, methanesulfonate, benzenesulfonate, toluenesulfonate, chloride, bromide, iodide, sulfate, phosphate, or the like.

Suitable pharmaceutically acceptable salts of the object compound [I]are conventional non-toxic salts and include a metal salt such as an alkali metal salt [e.g. sodium salt, potassium salt, etc.]and an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N'-dibenzylethylenediamine salt, etc.], an organic acid salt [e.g. formate, acetate, trifluoroacetate, maleate, tartrate, methanesulfonate, benzenesulfonate, toluenesulfonate, etc.], an inorganic acid salt [e.g. hydrochloride, hydrobromide, sulfate, phosphate, etc.], a salt with an amino acid [e.g. arginine salt, aspartic acid salt, glutamic acid salt, etc.], and the like.

Preferred embodiments of the object compound [I] are as follows.

Preferred embodiment of $R^1$ is amino,
$R^2$ is lower alkyl [more preferably ($C_1$-$C_4$)alkyl] or lower alkenyl [more preferably ($C_2$-$C_4$)alkenyl, most preferably propenyl],
$R^3$ is lower alkyl [more preferably ($C_1$-$C_4$)alkyl, most preferably methyl], hydroxy(lower)alkyl [more preferably hydroxy($C_1$-$C_4$)alkyl, most preferably hydroxyethyl] or acyloxy(lower)alkyl [more preferably carbamoyloxy(lower)alkyl or lower alkanoyloxy(lower)alkyl, most preferably carbamoyloxy($C_1$-$C_4$)alkyl or lower alkanoyloxy($C_1$-$C_4$)alkyl],
$R^4$ is amino, acylamino [more preferably carbamoylamino or lower alkanoylamino], lower alkylamino, carboxy(lower)alkylamino or N-[protected carboxy(lower)alkyl]amino [more preferably esterified carboxy(lower)alkylamino, most preferably lower alkoxycarbonyl(lower)alkylamino],
$R^7$ is hydrogen or lower alkyl [more preferably ($C_1$-$C_4$)alkyl, most preferably methyl].

The processes for preparing the object compound of the present invention are explained in detail in the following.

Process 1

The compound [I] or a salt thereof can be prepared by reacting the compound [II] or its reactive derivative at the amino group or a salt thereof with the compound [III] or its reactive derivative at the carboxy group or a salt thereof.

Suitable reactive derivative at the amino group of the compound [II] may include Schiff's base type imino or its tautomeric enamine type isomer formed by the reaction of the compound [II] with a carbonyl compound such as aldehyde, ketone or the like; a silyl derivative formed by the reaction of the compound [II] with a silyl compound such as bis(trimethylsilyl)acetamide, mono(trimethylsilyl)acetamide [e.g. N-(trimethylsilyl)acetamide], bis(trimethylsilyl)urea or the like; a derivative formed by reaction of the compound [II] with phosphorus trichloride or phosgene, and the like.

Suitable salts of the compound [II] and its reactive derivative can be referred to the ones as exemplified for the compound [I].

Suitable reactive derivative at the carboxy group of the compound [III] may include an acid halide, an acid anhydride, an activated amide, an activated ester, and the like. Suitable examples of the reactive derivatives may be an acid chloride; an acid azide; a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole or tetrazole; or an activated ester [e.g. cyanomethyl ester, methoxymethyl ester, dimethyliminomethyl [$(CH_3)_2\overset{+}{N}$=CH-] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the kind of the compound [III] to be used.

Suitable salts of the compound [III] and its reactive derivative can be referred to the ones as exemplified for the compound [I].

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound [III] is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonylbis-(2-methylimidazole); pentamethyleneketene-N-cyclohexylimine; diphenylketene-N-cyclohexylimine; ethoxyacetylene; 1-alkoxy-1- chloroethylene; trialkyl phosphite; ethyl polyphosphate; isopropyl polyphosphate; phosphorus oxychloride (phosphoryl chloride); phosphorus trichloride; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as an alkali metal bicarbonate, tri(lower)alkylamine, pyridine, N-(lower)alkylmorpholine, N,N-di(lower)alkylbenzylamine, or the like.

The reaction temperature is not critical, and the reaction is usually carried out under cooling to warming.

Process 2

The compound [Ib] or a salt thereof can be prepared by subjecting the compound [Ia] or a salt thereof to elimination reaction of the carboxy protective group.

Suitable method of this elimination reaction may include conventional one such as hydrolysis, reduction and the like.

(i) For Hydrolysis :

The hydrolysis is preferably carried out in the presence of a base or an acid including Lewis acid. Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0]-undec-7-ene, or the like.

Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, etc.]. The elimination using Lewis acid such as trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

(ii) For Reduction :

Reduction is carried out in a conventional manner, including chemical reduction and catalytic reduction.

Suitable reducing agents to be used in chemical reduction are a combination of a metal (e.g. tin, zinc, iron, etc.) or metallic compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g. platinum plate, spongy platinum, platinum black, colloidal platinum, platinum oxide, platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced iron, Raney iron, etc.), copper catalysts (e.g. reduced copper Raney copper, Ullman copper ,etc.) and the like. The reduction is usually carried out in a conventional solvent which does not adversely influence the reaction such as water, methanol, ethanol, propanol, N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to warming.

Process 3

The compound [Id] or a salt thereof can be prepared by subjecting the compound [Ic] or a salt thereof to elimination reaction of the hydroxy protective group. This reaction can be carried out in a similar manner to that of the aforementioned Process 2, and therefore the reagents to be used and the reaction conditions (e.g., solvent, reaction temperature, etc.) can be referred to those of the Process 2.

Processes A and B for the preparation of the starting compounds are explained in detail in the following.

Process A—①

The compound [VI] or a salt thereof can be prepared by reacting the compound [IV] or a salt thereof with the compound [V] or a salt thereof.

Suitable salts of the compounds [V] and [VI] can be referred to the ones as exemplified for the compound [I].

The present reaction may be carried out in a solvent such as water, phosphate buffer, acetone, chloroform, acetonitrile, nitrobenzene, methylene chloride, ethylene chloride, formamide, N,N-dimethylformamide, methanol, ethanol, diethyl ether, tetrahydrofuran, dimethyl sulfoxide, or any other organic solvent which does not adversely affect the reaction, preferably in ones having strong polarities. Among the solvents, hydrophilic solvents may be used in a mixture with water. When the compound [V] is in liquid, it can also be used as a solvent. The reaction is preferably conducted in the presence of a base, for example, inorganic base such as alkali metal hydroxide, alkali metal carbonate, alkali metal bicarbonate, organic base such as trialkylamine, and the like. The reaction temperature is not critical, and the reaction is usually carried out at ambient temperature, under warming or under heating. The present reaction is preferably carried out in the presence of alkali metal halide [e.g. sodium iodide, potassium iodide, etc.], alkali metal thiocyanate [e.g. sodium thiocyanate, potassium thiocyanate, etc.] or the like.

Anion $X^\ominus$ may be the one derived from a leaving group Y and may be the other one converted therefrom by a conventional method.

Process A—②

The compound [II] or a salt thereof can be prepared by subjecting the compound [VI] or a salt thereof to elimination reaction of the amino protective group in $R^5$ and the carboxy protective group in $R^6$.

This reaction is carried out in accordance with a conventional method such as hydrolysis or the like.

The hydrolysis is preferably carried out in the presence of a base or an acid including Lewis acid. Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, or the like. Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid,, hydrogen chloride, hydrogen bromide, etc.]. The elimination using Lewis acid such as trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

The present invention includes within the scope of the invention the case that protected amino in $R^4$ is transformed into amino during this reaction.

Process B

The compound [IIb] or a salt thereof can be prepared by subjecting the compound [IIa] to elimination reaction 1, of the amino protective group in $R_a^4$. This reaction can be carried out in a similar manner to that of the aforementioned Process A - ②, and therefore the reagents to be used and the reaction conditions (e.g., solvent, reaction temperature, etc.) can be referred to those of the Process A - ②. The present invention includes within the scope of the invention the case that protected hydroxy(lower)alkyl in $R^3$ is transformed into hydroxy(lower)alkyl during this reaction.

The object compound [I] and pharmaceutically acceptable salts thereof are novel and exhibit high antimicrobial activity, inhibiting the growth of a wide variety of pathogenic microorganisms including Gram-positive and Gram-negative microorganisms and are useful as antimicrobial agents.

Now in order to show the utility of the object compound [I], the test data on MIC (minimal inhibitory concentration) of a representative compound of this invention are shown in the following.

Test Method

In vitro antibacterial activity was determined by the two-fold agar-plate dilution method as described below.

One loopful of an overnight culture of each test strain in Trypticase-soy broth ($10^6$ viable cells per ml) was streaked on heart infusion agar (HI-agar) containing graded concentrations of representative test compound, and the minimal inhibitory concentration (MIC) was expressed in terms of μg/ml after incubation at 37° C. for 20 hours.

Test Compound

7β-[2-(5-Amino-1,2,4-thiadiazol-3-yl)-2-methoxyiminoacetamido]-3-(3-amino-2-methyl-1-pyrazolio)-methyl- 3-cephem-4-carboxylate (syn isomer) (hereinafter referred to as Compound A)

Test Results

| Test strain | MIC (μg/ml) Test Compound A |
|---|---|
| E. coli 31 | 0.05 |

For therapeutic administration, the object compound [I] and pharmaceutically acceptable salts thereof of the present invention are used in the form of conventional pharmaceutical preparation which contains said compound as an active ingredient, in admixture with pharmaceutically acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade and the like.

If needed, there may be included in the above preparations auxiliary substances, stabilizing agents, wetting agents and other commonly used additives such as lactose, citric acid, tartaric acid, stearic acid, magnesium stearate, terra alba, sucrose, corn starch, talc, gelatin, agar, pectin, peanut oil, olive oil, cacao butter, ethylene glycol, and the like.

While the dosage of the compound [I] may vary from and also depend upon the age, conditions of the patient, a kind of diseases, a kind of the compound [I] to be applied, etc. In general amounts between 1 mg and about 4,000 mg or even more per day may be administered to a patient. An average single dose of about 50 mg, 100 mg, 250 mg, 500 mg, 1000 mg, 2000 mg of the object compounds [I] of the present invention may be used in treating diseases infected by pathogenic microorganisms.

The following Preparations and Examples are given for the purpose of illustrating the present invention in more detail.

Preparation 1

(1) A mixture of acetic anhydride (11.13 ml) and formic acid (5.93 ml) was stirred at ambient temperature for 30 minutes. To this solution was added 5-amino-1-(2-hydroxyethyl)pyrazole (5 g) under ice-cooling, and the mixture was stirred at 30°-40° C. for 1 hour. The reaction mixture was poured into a mixture of water, tetrahydrofuran and ethyl acetate and adjusted to pH 6 with aqueous sodium bicarbonate. The organic layer was separated, and the aqueous layer was extracted with a mixture of tetrahydrofuran and ethyl acetate for three times. The organic layers were combined, dried over magnesium sulfate and evaporated in vacuo to give 5-formamido-1-(2-formyloxyethyl)pyrazole (5.18 g).

IR (Nujol) : 3180, 1705, 1660 cm$^{-1}$

NMR (DMSO-d$_6$, δ) : 4.21–4.61 (4H, m), 6.11 and 6.34 (1H, each d, J=3Hz), 7.47 (1H, d, J=3Hz), 8.00 (1H, s), 8.33 (1H, s)

The following compound was obtained according to a similar manner to that of Preparation 1(1).

(2) 5-Formamido-1-(2-formyloxyethyl)-4-methylpyrazole IR (Nujol) : 3180, 1715, 1660 cm$^{-1}$ NMR (DMSO-d$_6$, δ) : 1.81 and 1.86 (3H, each s), 4.01–4.48 (4H, m), 7.25 and 7.40 (1H, each s), 8.06 (1H, s), 8.22 and 9.13 (1H, each s)

Preparation 2

5-Amino-1-(2-hydroxyethyl)pyrazole (10 g) was added to a mixture of acetic acid (50 ml) and water (100 ml). A solution of potassium cyanate (25.5 g) in water (80 ml) was added dropwise thereto under stirring at 34° C. The mixture was stirred at room temperature overnight.

The reaction mixture was added to ethyl acetate (200 ml). The mixture was adjusted to pH 8.0 with potassium carbonate and extracted with tetrahydrofuran. The extract was dried over magnesium sulfate, and the organic solvent was evaporated in vacuo to give an oily product. Acetone was added to the said oily product to give 5-carbamoylamino-1-(2-hydroxyethyl)pyrazole (3.76 g) as amorphous solid.

IR (Nujol) : 3400, 3200, 1670, 1570 cm$^{-1}$

NMR (DMSO-d$_6$δ) : 3.64 (2H, t, J=6Hz), 3.97 (2H, t, J=6Hz), 6.02 and 6.13 (1H, each d, J=2Hz), 7.20 and 7.27 (1H, each d, J=2Hz)

Preparation 3

Formic acid (2.09 ml) was added to acetic anhydride (4.17 ml) at room temperature and the mixture was stirred for 30 minutes at the same temperature. 5-Carbamoylamino-1-(2-hydroxyethyl)pyrazole (3.76 g) was added thereto under stirring and ice-cooling. The mixture was stirred for 2 hours at room temperature. The reaction mixture was evaporated in vacuo and diisopropyl ether was added thereto to give 5-carbamoylamino-1-(2-formyloxyethyl)pyrazole (4.15 g).

mp 102°–104° C.

IR (Nujol) : 3400, 3200, 1710, 1660, 1560, 1170 cm$^{-1}$

NMR (D$_2$O, δ) : 4.20 (2H, t, J=5Hz), 4.36 (2H, t, J=5Hz), 5.96 (1H, s), 6.02 and 6.13 (1H, each d, J=2Hz), 7.24 and 7.32 (1H, each d, J=2Hz) 8.06 and 8.24 (1H, each s)

Preparation 4

1-(2-Hydroxyethyl)-5-aminopyrazole (5 g) was added to acetic anhydride (14.7 ml) under stirring and ice-cooling, and pyridine (6.3 ml) was added thereto. The mixture was stirred for 2 hours at 25° C. The reaction mixture was added to a mixture of ethyl acetate (50 ml) and brine (50 ml). Then, the mixture was adjusted to pH 7.0 with an aqueous solution of sodium bicarbonate. The aqueous layer was extracted with a mixture of ethyl acetate and tetrahydrofuran. The extract was dried over magnesium sulfate. The magnesium sulfate was filtered off, and the filtrate was evaporated under reduced pressure to give 1-(2-acetoxyethyl)-5-acetylaminopyrazole (5.98 g).

mp : 83°–84° C.

IR (Nujol) : 3270, 1750, 1670, 1565 cm$^{-1}$

NMR (DMSO-d$_6$, δ) : 1.93 (3H, s), 2.03 (3H, s), 4.22 (4H, br s), 6.13 (1H, d, J=2Hz), 7.32 (1H, d, J=2Hz), 9.76 (1H, s)

Preparation 5

A mixture of acetic anhydride (44.5 ml) and formic acid (22.3 ml) was stirred at ambient temperature for an hour. To this mixture was added 1-(2-hydroxyethyl)-5-aminopyrazole (30 g) at 0°–10° C., and the mixture was stirred under ice-cooling for 30 minutes. The mixture was poured into ice-cold water, adjusted to pH 10.5 with 40% aqueous potassium carbonate, and stirred under ice-cooling for 30 minutes. The mixture was extracted with a mixture of tetrahydrofuran and ethyl acetate 6 times. The organic layer was dried over magnesium sulfate and evaporated in vacuo to give 1-(2-hydroxyethyl)-5-formamidopyrazole (30.8 g).

IR (Nujol) : 3230, 1695, 1570, 1540 cm$^{-1}$

NMR (DMSO-d$_6$, δ) : 3.62–3.95 (2H, m), 3.98–4.32 (2H, m), 6.22 and 6.36 (1H, each d, J=3Hz), 7.42 (1H, d, J=3Hz), 8.32 and 8.36 (1H, each s)

Preparation 6

To a suspension of 5-formamido-1-(2-hydroxyethyl)-pyrazole (1 g) in acetonitrile (50 ml) was added dropwise chlorosulfonyl isocyanate (0.77 ml) at −15° C.~−20° C. The mixture was stirred for 3 hours under ice-cooling. To the reaction mixture was added water (1 ml) and kept to stand overnight. The solution was adjusted to pH 7.5 with 5N-sodium hydroxide solution and then adjusted to pH 8.5 with 1N-sodium hydroxide solution. The organic layer was separated and the aqueous layer was extracted with tetrahydrofuran. The extract and said organic layer were combined and dried over magnesium sulfate. The solvent was distilled off and the residue was crystallized from ethyl acetate to give 5-amino-1-(2-carbamoyloxyethyl)pyrazole (0.60 g).

NMR (DMSO-d$_6$, δ) : 3.83–4.35 (4H, m), 4.80–5.18 (2H, broad s), 5.32 (1H, d, J=3Hz), 6.33–6.87 (2H, broad s), 7.08 (1H, d, J=3Hz)

Preparation 7

5-Formamido-1-(2-carbamoyloxyethyl)pyrazole (3.69 g) was obtained from 5-amino-1-(2-carbamoyloxyethyl)pyrazole (3.3 g) according to a similar manner to that of Preparation 5.

NMR (DMSO-d$_6$, δ) : 4.22 (4H, s), 6.17–6.40 (1H, m), 6.40–6.63 (2H, m), 7.30–7.53 (1H, m), 8.13–8.47 (1H, m).

Preparation 8

(1) To a solution of 5-formamido-1-methylpyrazole in N,N-dimethylformamide (50 ml) was sodium hydride (1.6 g) under ice-cooling. Then, to the mixture was added methyl iodide (2.5 ml) at the same condition. The mixture was stirred for 1 hour under ice-cooling. To the reaction mixture was added a mixture of ethyl acetate (500 ml) and water (100 ml). The organic layer was separated, and the aqueous layer was extracted with ethyl acetate (50 ml×2). The organic solution was dried over magnesium sulfate. The solvent was distilled off and the residue was subjected to a column chromatography on silica gel using a mixture of ethyl acetate and diisopropyl ether (3:1) as an eluent. Fractions containing the object compound were collected and evaporated in vacuo to give 5-(N-formyl-N-methylamino)-1-methylpyrazole (2.5 g).

IR (Nujol) : 1660–1680, 1550, 1320 cm$^{-1}$

NMR (DMSO-d$_6$, δ) : 3.07 (3H, s), 3.67 (3H, s), 6.28 (1H, d, J=2Hz), 7.44 (1H, d, J=2Hz), 8.20 (1H, s)

The following compound was obtained according to a similar manner to that of Preparation 8(1).

(2) 5-(N-Formyl-N-methoxycarbonylmethylamino)-1-methylpyrazole

NMR (CDCl$_3$δ) : 3.68 (3H, s), 3.77 (3H, s), 4.26 (2H, s), 6.16 (1H, d, J=3Hz), 7.39 (1H, d, J=3Hz), 8.15 (1H, s)

Preparation 9

(1) To a mixture of benzhydryl 7β-tert-butoxycarbonylamino-3-chloromethyl-3-cephem-4-carboxylate (20 g) and sodium iodide (5.82 g) in N,N-dimethylformamide (20 ml) was added 5-formamido-1-(2-formyloxyethyl)pyrazole (21.34 g) at ambient temperature. After being stirred for 24 hours at the same temperature, the mixture was poured into a mixture of water and ethyl acetate. The organic layer was separated and washed with water, aqueous sodium chloride solution, and dried over magnesium sulfate. The solution was evaporated in vacuo to give benzhydryl 7β-tert-butoxycarbonylamino-3-[3-formamido-2-(2-formyloxyethyl)-1-pyrazolio]methyl-3-cephem-4-carboxylate iodide (29.6 g).

IR (Nujol) : 1780, 1720 cm$^{-1}$

NMR (DMSO-d$_6$δ) : 1.49 (9H, s), 3.43 (2H, br s), 4.14–4.38 (2H, m), 4.52–4.73 (2H, m), 5.15 (1H, d, J=5Hz), 5.40 (2H, br s), 5.67 (1H, dd, J=5, 8Hz), 6.88 (1H, s), 7.02 (1H, d, J=3Hz), 7.18–7.52 (10H, m), 7.94 (1H, d, J=8Hz), 7.99 (1H, s), 8.27 (1H, d, J=3Hz), 8.51 (1H, br s)

The following compounds were obtained according to a similar manner to that of Preparation 9(1).

(2) Benzhydryl 7δ-tert-butoxycarbonylamino-3-[3-formamido-2-(2-formyloxyethyl)-4-methyl-1-pyrazolio]methyl-3-cephem-4-carboxylate iodide IR (Nujol) : 3250, 1780, 1710, 1680 cm$^{-1}$ NMR (DMSO-d$_6$, δ) : 1.53 (9H, s), 1.97 (3H, s), 3.51 (2H, br s), 4.04–4.42 (2H, m), 4.52–4.78 (2H, m), 5.08 (1H, d, J=5Hz), 5.39 (2H, br s), 5.61 (1H, dd, J=5, 8Hz), 6.86 (1H, s), 7.08–7.52 (10H, m), 7.93 (1H, s), 8.18 (1H, s), 8.34 (1H, s), 9.12 (1H, s)

(3) Benzhydryl 7β-tert-butoxycarbonylamino-3-[3-carbamoylamino-2-(2-formyloxyethyl)-1-pyrazolio]methyl-3-cephem-4-carboxylate iodide IR (Nujol) : 3300, 1780, 1710 cm$^{-1}$ NMR (DMSO-d$_6$, δ) : 1.43 (9H, s), 3.5–3.8 (2H, m), 4.1–4.6 (4H, m), 5.14 (1H, d, J=5Hz), 5.33 (2H, s), 5.60 (1H, dd, J=8Hz, 5Hz), 6.66 (1H, s), 6.86 (1H, d, J=3Hz), 7.1–7.5 (10H, m), 7.93 (1H, d, J=8Hz), 8.00 (1H, s), 8.08 (1H, d, J=3Hz)

(4) Benzhydryl 7β-tert-butoxycarbonylamino-3-[3-acetamido-2-(2-acetoxyethyl)-1-pyrazolio]methyl-3-cephem-4-carboxylate iodide IR (Nujol) : 1780, 1720, 1230 cm$^{-1}$ NMR (DMSO-d$_6$, δ) : 1.41 (9H, s), 1.86 (3H, s), 2.25 (3H, s), 3.40 (2H, br s), 4–4.4 (4H, m), 5.12 (1H, d, J=5Hz), 5.37 (2H, s), 5.60 (1H, dd, J=8Hz, 5Hz), 6.85 (1H, s), 7.24 (1H, d, J=3Hz), 7.1–7.6 (10H, m), 7.90 (1H, d, J=8Hz), 8.21 (1H, d, J=3Hz), 11.17 (1H, s)

(5) Benzhydryl 7β-tert-butoxycarbonylamino-3-[2-(2-carbamoyloxyethyl)-3-formamido-1-pyrazolio)methyl-3-cephem-4-carboxylate iodide (6) Benzhydryl 7-tert-butoxycarbonylamino-3-[3-(N-formyl-N-methylamino)-2-methyl-1-pyrazolio]methyl-3-cepham-4-carboxylate iodide NMR (DMSO-d$_6$, δ) : 1.38 (9H, s), 3.29 (3H, s), 3.68 (3H, s), 3.07–3.77 (2H, m), 5.18 (1H, d, J=5Hz), 5.35–5.75 (3H, m), 6.90 (1H, s), 7.01 (1H, d, J=2Hz), 7.08–7.60 (10H, m), 8.02 (1H, d, J=8Hz), 8.35 (1H, s), 8.43 (1H, d, J=2Hz)

(7) Benzhydryl 7-tert-butoxycarbonylamino-3-[3-(N-formyl-N-methoxycarbonylmethylamino)-2-methyl-1-pyrazolio]-methyl-3-cephem-4-carboxylate iodide IR (Nujol) : 3300, 1780, 1620 cm$^{-1}$ Preparation 10

(1) To a solution of benzhydryl 7β-tert-butoxycarbonylamino-3-[3-formamido-2-(2-formyloxyethyl)-1-pyrazolio]methyl-3-cephem-4-carboxylate iodide (29.5 g) and anisole (30 ml) in methylene chloride (90 ml) was added dropwise trifluoroacetic acid (60 ml) under ice-cooling. After being stirred for 1 hour at ambient temperature, the mixture was poured into a mixture of diisopropyl ether (600 ml) and ethyl acetate (600 ml). The resultant precipitate was collected by filtration to give di(trifluoroacetic acid) salt of 7β-amino-3-[3-formamido-2-(2-formyloxyethyl)-1-pyrazolio]methyl-3-cephem-4-carboxylate (22.7 g).

IR (Nujol) : 1780, 1715, 1660 cm$^{-1}$

NMR (DMSO-d$_6$, δ) : 3.53 (2H, br s), 4.28–4.56 (2H, m), 4.78–4.99 (2H, m), 5.29 (2H, br s), 5.53 (2H, br s), 7.14 (1H, d, J=3Hz), 8.22 (1H, s), 8.46 (1H, d, J=3Hz), 8.63 (1H, s)

The following compounds were obtained according to a similar manner to that of Preparation 10(1).

(2) Di(trifluoroacetic acid) salt of 7β-amino-3-[3-formamido-2-(2-formyloxyethyl)-4-methyl-1-pyrazolio]-methyl-3-cephem-4-carboxylate IR (Nujol) : 1780, 1710, 1670 cm$^{-1}$ NMR (DMSO-d$_6$, δ) : 1.98 (3H, s), 3.49 (2H, br s), 4.22–4.48 (2H, m), 4.61–4.87 (2H, m), 5.18 (2H, br s), 5.46 (2H, br s), 8.05 (1H, s), 8.23 (1H, s), 8.35 (1H, s)

(3) Di(trifluoroacetic acid) salt of 7β-amino-3-[3-carbamoylamino-2-(2-formyloxyethyl)-1-pyrazolio]methyl-3-cephem-4-carboxylate IR (Nujol) : 3400, 1780, 1700, 1560 cm$^{-1}$ NMR (DMSO-d$_6$, δ) : 3.46 (2H, br s), 4.2–4.6 (4H, m), 5.22 (2H, m), 5.40 (2H, s), 6.92 (1H, d, J=3Hz), 8.13 (1H, s), 8.20 (1H, d, J=3Hz)

(4) Di(trifluoroacetic acid) salt of 7β-amino-3-[3-acetamido-2-(2-acetoxyethyl)-1-pyrazolio]methyl-3-cephem-4-carboxylate IR (Nujol) : 1780, 1660, 1190 cm$^{-1}$ NMR (DMSO-d$_6$, δ) : 1.95 (3H, s), 2.23 (3H, s), 3.46 (2H, br s), 4.1–4.4 (4H, m), 5.20 (2H, m), 5.46 (2H, s), 7.01 (1H, d, J=3Hz), 8.27 (1H, d, J=3Hz), 11.17 (1H, s)

(5) Di(trifluoroacetic acid) salt of 7β-amino-3-[2-(2-carbamoyloxyethyl)-3-formamido-1-pyrazolio]methyl-3-cephem-4-carboxylate (6) Di(trifluoroacetic acid) salt of 7β-amino-3-[3-(N-formyl-N-methylamino)-2-methyl-1-pyrazolio]methyl-3-cephem-4-carboxylate NMR (D$_2$O, δ) : 3.46 (3H, s), 3.87, 4.00 (total 3H, each s), 3.13–3.77 (2H, m), 5.05–5.47 (4H, m), 6.89 (1H, d, J=2Hz), 8.32 (1H, d, J=2Hz), 8.36 (1H, s)

(7) Di(trifluoroacetic acid) salt of 7β-amino-3-[3-(N-formyl-N-methoxycarbonylmethylamino)-2-methyl-1-pyrazolio]methyl-3-cephem-4-carboxylate IR (Nujol) : 3300, 1780, 1610 cm$^{-1}$ Preparation 11

(1) Concentrated hydrochloric acid (5.67 ml) was added to a mixture of di(trifluoroacetic acid) salt of 7β-amino-3-[3-formamido-2-(2-formyloxyethyl)-1-pyrazolio]methyl-3-cephem-4-carboxylate (10 g) in methanol (50 ml ) at ambient temperature. After being stirred at the same temperature for 3 hours, the mixture was added dropwise to ethyl acetate (500 ml). The resultant precipitate was collected by filtration to give 7β-amino-3-[3-amino-2-(2-hydroxyethyl)-1-pyrazolio]-methyl-3-cephem-4-carboxylate trihydrochloride (6.1 g).

IR (Nujol) : 3250, 1770, 1700, 1625 cm$^{-1}$

NMR (DMSO-d$_6$, δ) : 3.43 (2H, br s), 3.52–3.88 (2H, m), 4.18–4.48 (2H, m), 5.28 (2H, br s), 5.37 (2H, br s), 5.97 (1H, d, J=3Hz), 8.18 (1H, d, J=3Hz)

The following compounds were obtained according to a similar manner to that of Preparation 11(1).

(2) 7β-Amino-3-[3-amino-2-(2-hydroxyethyl)-4-methyl-1-pyrazolio]methyl-3-cephem-4-carboxylate trihydrochloride NMR (DMSO-d$_6$, δ) : 1.94 (3H, s), 3.39 (2H, br s), 3.47–3.78 (2H, m), 4.06–4.42 (2H, m), 5.21 (4H, br s), 7.87 (1H, s)

(3) 7β-Amino-3-[3-carbamoylamino-2-(2-hydroxyethyl)-1-pyrazolio]methyl-3-cephem-4-carboxylate dihydrochloride IR (Nujol) : 3300, 1770, 1700, 1560 cm$^{-1}$ NMR (DMSO-d$_6$, δ) : 3.41 (2H, br s), 3.6–3.8 (4H, m), 5.20 (2H, m), 5.43 (2H, s), 6.85 (1H, d, J=3Hz), 8.20 (1H, d, J=3Hz)

(4) 7β-Amino-3-[3-amino-2-(2-carbamoyloxyethyl)-1pyrazolio]methyl-3-cephem-4-carboxylate trihydrochloride (5) 7β-Amino-3-[2-methyl-3-methylamino-1-pyrazolio]methyl-3-cephem-4-carboxylate trihydrochloride NMR (D$_2$O-NaHCO$_3$, δ) : 2.93 (3H, s), 3.25–3.38 (2H, m), 3.63 (3H, s), 5.07–5.33 (4H, m), 5.97 (1H, d, J=2Hz), 7.89 (1H, d, J=2Hz)

(6) 7β-Amino-3-[2-methyl-3-methoxycarbonylmethylamino-1-pyrazolio]methyl-3-cephem-4-carboxylate trihydrochloride IR (Nujol) : 3200–3350, 1780, 1610 cm$^{-1}$

EXAMPLE 1

To a solution of 7β-amino-3-[3-amino-2-(2-hydroxyethyl)-1-pyrazolio]methyl-3-cephem-4-carboxylate trihydrochloride (2 g) and N-(trimethylsilyl)acetamide (5.85 g) in tetrahydrofuran (40 ml) was added (Z)-2-(5-amino-1,2,4-thiadiazol-3-yl)-2-allyloxyiminoactyl chloride hydrochloride (1.26 g) under ice-cooling. After being stirred for 1 hour at the same temperature, the reaction mixture was poured into diisopropyl ether (200 ml). The resulting precipitate was collected by filtration, dissolved in water (100 ml) and adjusted to pH 2.0 with 5% sodium bicarbonate solution. This solution was subjected to column chromatography on macroporous non-ionic adsorption resin "Diaion HP-20" (Trademark : prepared by Mitsubishi Chemical Industries). The desired compound was eluted with 10% isopropyl alcohol and lyophilized to give 7β-[2-(5-amino-1,2,4-thiadiazol-3-yl)-2-allyloxyiminoacetamido]-3-[3-amino-2-(2-hydroxyethyl)-1-pyrazolio]methyl-3-cephem-4-carboxylate (syn isomer) (1.07 g).

IR (Nujol) : 3150, 1760, 1660 cm$^{-1}$

NMR (DMSO-d$_6$, δ) : 2.90 and 3.23 (2H, ABq, J=18Hz), 3.68 (2H, br s), 4.38 (2H, m), 4.63 (2H, d, J=5Hz), 5.02 (1H, d, J=5Hz), 5.09–5.47 (2H, m), 5.04 and 5.33 (2H, ABq, J=15Hz), 5.64 (1H, dd, J=5, 8Hz), 5.78–6.16 (1H, m), 5.81 (1H, d, J=3Hz), 7.26 (2H, br s), 8.08 (1H, d, J=3Hz), 8.10 (2H, br s), 9.50 (1H, d, J=8Hz)

EXAMPLE 2

The following compounds were obtained according to a similar manner to that of Example 1.

(1) 7β-[2-(5-Amino-1,2,4-thiadiazol-3-yl)-2-methoxyiminoacetamido]-3-(2-methyl-3-amino-1-pyrazolio)-methyl-3-cephem-4-carboxylate (syn isomer)

IR (Nujol) : 3580, 3310, 3200, 1760, 1670, 1615, 1580 cm$^{-1}$

NMR (DMSO-d$_6$-D$_2$O, δ) : 2.97, 3.23 (2H, ABq, J=18Hz), 3.68 (3H, s), 5.01 (1H, d, J=5Hz), 4.98, 5.28 (2H, ABq, J=15Hz), 5.66 (1H, d, J=5Hz), 5.85 (1H, d, J=3Hz), 8.01 (1H, d, J=3Hz)

(2) 7β-2-(5-Amino-1,2,4-thiadiazol-3-yl)-2-methoxyiminoacetamido]-3-[2-(2-hydroxyethyl)-3-amino-1-pyrazolio]methyl-3-cephem-4-carboxylate (syn isomer)

IR (Nujol) : 3150–3300, 1760, 1580–1660 cm$^{-1}$

NMR (DMSO-d$_6$, δ) : 2.92, 3.25 (2H, ABq, J=18Hz), 3.40–3.77 (3H, m), 3.80 (3H, s), 4.14–4.70 (2H, m), 4.90–5.42 (2H, m), 5.63 (1H, dd, J=5Hz, 8Hz), 5.83 (1H, d, J=3Hz), 7.17–7.57 (2H, br s), 8.08 (1H, d, J=3Hz), 7.93–8.30 (2H, br s), 9.49 (1H, d, J=8Hz)

(3) 7β-[2-(5-Amino-1,2,4-thiadiazol-3-yl)-2-allyloxyiminoacetamido]-3-[3-amino-2-(2-hydroxyethyl)-4-methyl-1-pyrazolio]methyl-3-cephem-4-carboxylate (syn isomer)

IR (Nujol) : 3250, 1760, 1640, 1600 cm$^{-1}$

NMR (D$_2$O, δ) : 1.96 (3H, s), 3.03 and 3.33 (2H, ABq, J=18Hz), 3.69–3.33 (2H, m), 4.17–4.41 (2H, m), 4.78 (2H, d, J=5Hz), 5.03 (1H, d, J=5Hz), 5.04–5.48 (4H, m), 5.72–6.21 (1H, m), 5.81 (1H, d, J=5Hz), 7.68 (1H, s)

(4) 7β-[2-(5-Amino-1,2,4-thiadiazol-3-yl)-2-allyloxyiminoacetamido]-3-[3-carbamoylamino-2-(2-hydroxyethyl)-1-pyrazolio]methyl-3-cephem-4-carboxylate (syn isomer)

IR (Nujol) : 3300, 1770, 1700, 1560 cm$^1$

NMR (D$_2$O, δ) : 3.07 (1H, d, J=18Hz), 3.40 (1H, d, J=18Hz), 3.84 (4H, m), 4.74 (2H, d, J=5Hz), 5.20 (1H, d, J=5Hz), 5.25 (2H, s), 5.1–5.5 (2H, m), 5.79 (1H, d, J=5Hz), 5.9–6.4 (1H, m), 6.74 (1H, d, J=3Hz), 8.04 (1H, d, J=3Hz)

(5) 7β-[2-(5-Amino-1,2,4-thiadiazol-3-yl)-2-methoxyiminoacetamido]-3-[3-amino-2-(2-carbamoyloxyethyl)-1pyrazolio]methyl-3-cephem-4-carboxylate (syn isomer)

IR (Nujol) : 3300, 1760, 1710, 1590, 1520 cm$^{-1}$

NMR (D$_2$O, δ) : 3.07 (1H, d, J=18Hz), 3.42 (1H, d, J=18Hz), 4.06 (3H, s), 4.17–4.60 (4H, m), 4.70–5.43 (3H, m), 5.83 (1H, d, J=5Hz), 5.94 (1H, d, J=3Hz), 7.87 (1H, d, J=3Hz)

(6) 7β-[2-(5-Amino-1,2,4-thiadiazol-3-yl)-2-allyloxyiminoacetamido]-3-[3-amino-2-(2-carbamoyloxyethyl)-1-pyrazolio]methyl-3-cephem-4-carboxylate (syn isomer)

IR (Nujol) : 3300, 1770, 1710, 1600 cm$^{-1}$

NMR (D$_2$O, δ) : 3.00–3.77 (2H, m), 4.27–4.67 (4H, m), 4.67–5.63 (7H, m), 5.96 (1H, d, J=5Hz), 6.06 (1H, d, J=3Hz), 7.99 (1H, d, J=3Hz)

(7) 7β-[2-(5-Amino-1,2,4-thiadiazol-3-yl)-2-allyloxyiminoacetamido]-3-[2-methyl-3-methylamino-1-pyrazolio]methyl-3-cephem-4-carboxylate (syn isomer)

IR (Nujol) : 3200–3300, 1770, 1670, 1610, 1520 cm$^{-1}$

NMR (D$_2$O, δ) : 2.88 (3H, s), 3.58 (3H, s), 3.03–3.33 (2H, m), 4.50–4.87 (2H, m), 4.93–5.48 (3H, m), 5.70–5.97 (2H, m), 7.84 (1H, d, J=3Hz)

(8) 7β-[2-(5-Amino-1,2,4-thiadiazol-3-yl)-2-methoxyiminoacetamido]-3-(2-methyl-3-methylamino-1-pyrazolio)methyl-3-cephem-4-carboxylate (syn isomer)

IR (Nujol) : 3200–3300, 1760, 1660, 1610, 1520 cm$^{-1}$

NMR (D₂O, δ) : 2.89 (3H, s), 3.58 (3H, s), 4.04 (3H, s), 3.03–3.30 (2H, m), 4.93–5.25 (2H, m), 5.77–5.97 (2H, m), 7.85 (1H, d, J=3Hz)

EXAMPLE 3

To a solution of di(trifluoroacetic acid) salt of 7β-amino-3-[3-acetamido-2-(2-acetoxyethyl)-1-pyrazolio]-methyl-3-cephem-4-carboxylate (1g) and N-(trimethylsilyl)acetamide (2.01 g) in dichloromethane (20 ml) was added (Z)-2-(5-amino-1,2,4-thiadiazol-3-yl)-2-allyloxyiminoacetyl chloride hydrochloride (0.520 g) under stirring and ice-cooling. The mixture was stirred for one hour at room temperature. The reaction mixture was added to ether under stirring and ice-cooling. The produced amorphous solid was dried in vacuo and dissolved in water. The aqueous solution was adjusted to pH 13 with 1N aqueous sodium hydroxide under stirring at −3∼0° C. and stirred for 2 hours at the same temperature. The aqueous solution was adjusted to pH 2 with 1N hydrochloric acid and subjected to column chromatography on Diaion HP-20 and the elution was carried out with 10% aqueous isopropyl alcohol. The fractions containing the object compound were combined, concentrated to remove isopropyl alcohol and lyophilized to give 7β-[2-(5-amino-1,2,4-thiadiazol-3-yl)-2-allyloxyiminoacetamido]-3-[3-acetamido-2-(2-hydroxyethyl)-1-pyrazolio]methyl-3-cephem-4-carboxylate (syn isomer) (222 mg).

mp : 150° C. (dec.)

IR (Nujol) : 3200, 1770, 1660, 1600 cm⁻¹

NMR (D₂O, δ) : 2.22 (3H, s), 3.08 (1H,d, J=18Hz), 3.42 (1H, d, J=18Hz), 3.7–4.0 (4H, m), 4.74 (2H, d, J=6Hz), 5.20 (1H, d, J=5Hz), 5.30 (2H, s), 5.1–5.5 (2H, m), 5.81 (1H, d, J=5Hz), 5.8–6.4 (1H, m), 6.85 (1H, d, J=3Hz), 8.11 (1H, d, J=3Hz)

EXAMPLE

To a solution of 7β-amino-3-[2-methyl-3-methoxycarbonylmethylamino-1-pyrazolio]methyl-3-cephem-4-carboxylate trihydrochloride (0.7 g) and N-(trimethylsilyl)acetamide (1.87 g) in tetrahydrofuran (14 ml) was added (Z)-2-(5-amino-1,2,4-thiadiazol-3-yl)-2-methoxyiminoacetyl chloride hydrochloride (0.37 g) under ice-cooling and the mixture was stirred at room temperature for 2 hours. The reaction mixture was poured into ethyl acetate (140 ml) and the resultant powder was collected by filtration. The powder was dissolved in ice-water and adjusted to pH 13 with 1N aqueous sodium hydroxide. After stirring for 20 minutes under ice-cooling, the solution was adjusted to pH 2 with 3N hydrochloric acid and subjected to column chromatography on "Diaion HP-20" using 5% aqueous isopropyl alcohol as an eluent. Fractions containing the object compound were combined, evaporated in vacuo to remove isopropyl alcohol and lyophilized to give 7β-[2-(5-amino-1,2,4-thiadiazol-3-yl)-2-methoxyiminoacetamido]-3-(3-carboxymethylamino-2-methyl-1-pyrazolio)methyl-3-cephem-4-carboxylate (syn isomer) (0.24 g).

IR (Nujol) : 3250, 1760, 1670, 1610, 1520 cm⁻¹

NMR (D₂O, δ) : 3.10 and 3.38 (2H, ABq, J=18Hz), 3.67 (3H, s), 3.83 (2H, s), 4.06 (3H, s), 4.97 and 5.28 (2H, ABq, J=14Hz), 5.18 (1H, d, J=5Hz), 5.82 (1H, d, J=5Hz), 5.84 (1H, d, J=3Hz), 7.85 (1H, d, J=3Hz)

EXAMPLE 5

The following compound was obtained according to a similar manner to that of Example 4.

7β-[2-(5-Amino-1,2,4-thiadiazol-3-yl)-2-allyloxyiminoacetamido]-3-(3-carboxymethylamino-2-methyl-1-pyrazolio)methyl- 3-cephem-4-carboxylate (syn isomer)

IR (Nujol) : 3300, 1770, 1670, 1610, 1520 cm⁻¹

NMR (D₂O-NaHCO₃, δ) : 3.10 and 3.38 (2H, ABq, J=18Hz), 3.67 (3H, s), 3.83 (2H, s), 4.67–4.93 (2H, m), 4.83–5.53 (2H, m), 5.19 (1H, d, J=5Hz), 5.70–6.23 (3H, m), 7.85 (1H, d, J=3Hz)

What we claim is:

1. A compound of the formula :

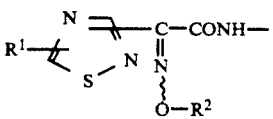

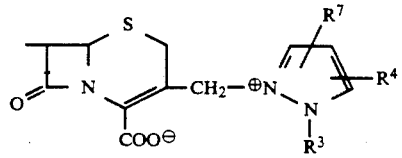

wherein $R^1$ is amino or protected amino, $R^2$ is lower alkyl or lower alkenyl, $R^3$ is lower alkyl, hydroxy(lower)alkyl or protected hydroxy(lower)alkyl, $R^4$ is amino, protected amino, lower alkylamino, protected lower alkylamino, carboxy(lower)alkylamino, N-[protected carboxy(lower)alkyl]amino and $R^7$ is hydrogen or lower alkyl, and a pharmaceutically acceptable salt thereof.

2. A compound of claim 1, wherein $R^3$ is lower alkyl, hydroxy(lower)alkyl carbamoyloxy(lower)alkyl or lower alkanoyloxy(lower)alkyl and $R^4$ is amino, carbamoylamino, lower alkanoylamino, lower alkylamino, carboxy(lower)alkylamino or esterified carboxy(lower)alkylamino.

3. A compound of claim 2, wherein $R^3$ is lower alkyl, hydroxy(lower)alkyl, carbamoyloxy(lower)alkyl or lower alkanoyloxy(lower)alkyl, $R^4$ is amino, carbamoylamino, lower alkanoylamino, lower alkylamino, carboxy(lower)alkylamino or lower alkoxycarbonyl(lower)alkylamino.

4. A compound of claim 3, wherein $R^1$ is amino, $R^2$ is lower alkyl or lower alkenyl, $R^3$ is lower alkyl, hydroxy(lower)alkyl or carbamoyloxy(lower)alkyl, $R^4$ is amino, carbamoylamino, lower alkanoylamino, lower alkylamino or carboxy(lower)alkylamino, and $R^7$ is hydrogen or lower alkyl.

5. A compound of claim 4, which is 7β-[2-(5-Amino-1,2,4-thiadiazol-3-yl)-2-methoxyiminoacetamido]-3-(3-amino-2-methyl-1-pyrazolio)methyl-3-cephem-4-carboxylate (syn isomer).

6. An antimicrobial pharmaceutical composition which comprises an effective amount of a compound of claim 1 or a pharmaceutically acceptable salt thereof in admixture with a pharmaceutically acceptable carrier.

7. A method for the treatment of infectious disease which comprises administering an effective amount of a compound of claim 1 or a pharmaceutically acceptable salt thereof to a human or animal.

8. A compound of claim 4, wherein $R^3$ is lower alkyl or hydroxy (lower) alkyl, $R^4$ is amino, and $R^7$ is hydrogen.

* * * * *

UNITED STATES PATENT AND TRADEMARK OFFICE
CERTIFICATE OF CORRECTION

PATENT NO. : 5,210,080
DATED : May 11, 1993
INVENTOR(S) : Takaya et al

It is certified that error appears in the above-indentified patent and that said Letters Patent is hereby corrected as shown below:

On the title page, after item [73] Assignee, the [*] Notice should read as follows:

--[*] Notice: The portion of the term of this patent subsequent to May 22, 2007, has been disclaimed. --.

Signed and Sealed this

Twenty-eighth Day of June, 1994

Attest:

BRUCE LEHMAN

*Attesting Officer*   *Commissioner of Patents and Trademarks*